United States Patent
Patrick et al.

(10) Patent No.: US 11,620,317 B2
(45) Date of Patent: Apr. 4, 2023

(54) FRAMEWORKS AND METHODOLOGIES FOR ENABLING SEARCHING AND/OR CATEGORISATION OF DIGITISED INFORMATION, INCLUDING CLINICAL REPORT DATA

(71) Applicant: HEALTH LANGUAGE ANALYTICS PTY LTD, Eveleigh (AU)

(72) Inventors: Jon Patrick, Sydney (AU); Pooyan Asgari, Sydney (AU); Min Li, Sydney (AU)

(73) Assignee: Health Language Analytics Pty Ltd, Eveleigh (AU)

( * ) Notice: Subject to any disclaimer, the term of this patent is extended or adjusted under 35 U.S.C. 154(b) by 0 days.

(21) Appl. No.: 15/740,218

(22) PCT Filed: Jun. 30, 2016

(86) PCT No.: PCT/AU2016/000235
§ 371 (c)(1),
(2) Date: Dec. 27, 2017

(87) PCT Pub. No.: WO2017/000019
PCT Pub. Date: Jan. 5, 2017

(65) Prior Publication Data
US 2018/0189381 A1 Jul. 5, 2018

(30) Foreign Application Priority Data

Jun. 30, 2015 (AU) .................................. 2015902540
Jun. 30, 2015 (AU) .................................. 2015902542

(51) Int. Cl.
| G06F 16/33 | (2019.01) |
| G06F 16/35 | (2019.01) |
| G06Q 10/10 | (2023.01) |
| G16H 15/00 | (2018.01) |

(Continued)

(52) U.S. Cl.
CPC .............. *G06F 16/33* (2019.01); *G06F 16/35* (2019.01); *G06F 40/242* (2020.01); *G06Q 10/10* (2013.01);
(Continued)

(58) Field of Classification Search
CPC ........ G16H 10/60; G16H 70/60; G16H 15/00; G06F 16/33; G06F 16/35; G06F 40/242; G16Z 99/00; G06Q 10/10
See application file for complete search history.

(56) References Cited

U.S. PATENT DOCUMENTS 6,915,254 B1 * 7/2005 Heinze .................... G06F 17/27
704/9
8,086,486 B2 * 12/2011 Hafner .................. G06Q 30/02
379/114.03

(Continued)

FOREIGN PATENT DOCUMENTS

WO WO2015/077898 A1 6/2015

*Primary Examiner* — Mark D Featherstone
*Assistant Examiner* — Ranjit P Doraiswamy
(74) *Attorney, Agent, or Firm* — Shay Glenn LLP

(57) ABSTRACT

The present disclosure relates to frameworks and methodologies for enabling categorisation and/or searching of digitised information, including clinical report data. Embodiments of the invention have been particularly developed to assist categorisation of digitised information, such as clinical report data, in a streamlined manner based on a pre existing set of classification codes. This, in some embodiments, enables the discovery and extraction of meaningful patterns from unstructured clinical reports. Further embodiments of the invention have been particularly developed to assist in the discovery and extraction of meaningful patterns from an unstructured set of digitised information such as unstructured clinical reports. While some embodiments will be described herein with particular reference to those appli- (Continued)

cations, it will be appreciated that the invention is not limited to such a field of use, and is applicable in broader contexts.

8 Claims, 7 Drawing Sheets

(51) Int. Cl.
    *G06F 40/242*     (2020.01)
    *G16H 70/60*     (2018.01)
    *G16Z 99/00*     (2019.01)
    *G16H 10/60*     (2018.01)

(52) U.S. Cl.
    CPC ............. *G16H 10/60* (2018.01); *G16H 15/00* (2018.01); *G16H 70/60* (2018.01); *G16Z 99/00* (2019.02)

(56) References Cited

U.S. PATENT DOCUMENTS

| | | | |
|---|---|---|---|
| 9,418,150 B2* | 8/2016 | Charlot | G06F 16/2365 |
| 2005/0240439 A1 | 10/2005 | Covit et al. | |
| 2009/0299977 A1 | 12/2009 | Rosales | |
| 2010/0179827 A1* | 7/2010 | McCallie, Jr. | G16H 10/60 |
| | | | 705/3 |
| 2015/0178874 A1 | 6/2015 | Harris et al. | |
| 2015/0379241 A1 | 12/2015 | Furst et al. | |
| 2016/0048655 A1* | 2/2016 | Maitra | G16H 70/40 |
| | | | 705/3 |
| 2016/0364532 A1* | 12/2016 | Honeycutt | G16H 10/60 |

* cited by examiner

FRAMEWORKS AND METHODOLOGIES FOR ENABLING SEARCHING AND/OR CATEGORISATION OF DIGITISED INFORMATION, INCLUDING CLINICAL REPORT DATA

FIELD OF THE INVENTION

The present invention relates to frameworks and methodologies for enabling categorisation and/or searching of digitised information, including clinical report data. Embodiments of the invention have been particularly developed to assist categorisation of digitised information, such as clinical report data, in a streamlined manner based on a pre-existing set of classification codes. This, in some embodiments, enables the discovery and extraction of meaningful patterns from unstructured clinical reports. Further embodiments of the invention have been particularly developed to assist in the discovery and extraction of meaningful patterns from an unstructured set of digitised information such as unstructured clinical reports. While some embodiments will be described herein with particular reference to those applications, it will be appreciated that the invention is not limited to such a field of use, and is applicable in broader contexts.

BACKGROUND

Any discussion of the background art throughout the specification should in no way be considered as an admission that such art is widely known or forms part of common general knowledge in the field.

A huge quantity of clinical record data is produced each and every day. Even for a relatively small medical facility, the task of categorising and organising clinical record data can be unwieldy. Furthermore, due to complexities of clinical language, text or keyword based searching of electronic records is limited in its efficacy.

SUMMARY OF THE INVENTION

It is an object of the present invention to overcome or ameliorate at least one of the disadvantages of the prior art, or to provide a useful alternative.

Although embodiments have been described and claimed by reference to application in fields where clinical report data is used, it should be appreciated that underlying inventions are necessarily rooted in computer technology, as opposed to abstract ideas and/or business innovations.

One embodiment provides a computer implemented method for enabling searching of clinical records, the method including:

A computer implemented method for enabling categorisation of clinical records, the method including:

identifying a set of user-generated text contained in a user interface object in a user interface environment;

processing the set of user-generated text based on a natural language processing engine, wherein the natural language processing engine leverages a clinical terminology knowledge base;

based on the processing, identifying a set of one or more suggested classification codes, wherein the classification codes are defined by a pre-existing clinical code structure;

causing display of a user interface component in the user interface environment, wherein the user interface component: (i) displays the identified set of one or more suggested classification codes; and (ii) enables a user to selectively confirm/reject one or more of the set of identified codes;

receiving input representative of the one or more of the set of identified codes selectively confirmed by the user; and providing a signal thereby to cause association of a clinical record including the set of user-generated text with the set of identified codes selectively confirmed by the user.

One embodiment provides a method wherein the user interface component is additionally configured to provide a search interface that enables a user to identify and selectively confirm one or more further codes, wherein the a signal causes association of a clinical record including the set of user-generated text with the set of identified codes selectively confirmed by the user and the one or more further codes.

One embodiment provides a method wherein, in response to an event whereby a user identifies and selectively confirms one or more further codes, a trigger is initiated thereby to cause updating of the natural language processing engine and/or clinical terminology knowledge base.

One embodiment provides a method including causing rendering of a graphical output that associates each identified suggested clinical classification code with a portion of the user-generated text.

One embodiment provides a method including causing rendering of a graphical output that associates each identified suggested clinical classification code with additional clinical code context.

One embodiment provides a method wherein the identification of suggested clinical classification codes is configured to identify a disease stage.

One embodiment provides a method wherein the user interface component is provided by a software application separate to a further software application in which the set of user generated text is contained.

One embodiment provides a computer implemented method for enabling searching of clinical records, the method including:

maintaining access to a database that includes data representative of clinical records, wherein each clinical record is pre-processed based upon a natural language processing engine thereby to associate the record with one or more clinical codes, wherein the clinical codes are defined in a clinical code hierarchical structure;

receiving a query from an interface that is configured enable user input of query parameters, wherein the query parameters include text-based concept-defining data;

processing the text-based concept-defining data based on a predefined protocol thereby to identify one or more clinical codes associated the concept-defining data; and identifying one or more clinical records that are associated with the same clinical codes as the concept-defining data.

One embodiment provides a computer implemented method including additionally associating with the concept-defining data one or more further clinical codes, wherein the one or more further clinical codes are sub-tree codes to the identified one or more clinical codes in the hierarchical structure.

One embodiment provides a computer implemented method wherein the interface is configured to enable the user to select whether or not to perform the process of additionally associating with the concept-defining data one or more further clinical codes, wherein the one or more further clinical codes are sub-tree codes to the identified one or more clinical codes in the hierarchical structure.

One embodiment provides a computer implemented method wherein there is a plurality of clinical code hierarchical structures.

One embodiment provides a computer implemented method wherein the interface is configured to enable the user to select one or more of the plurality of clinical code hierarchical structures for a given query.

One embodiment provides a computer program product for performing a method as described herein.

One embodiment provides a non-transitory carrier medium for carrying computer executable code that, when executed on a processor, causes the processor to perform a method as described herein.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the invention will now be described, by way of example only, with reference to the accompanying drawings in which.

DETAILED DESCRIPTION

Figure 1:
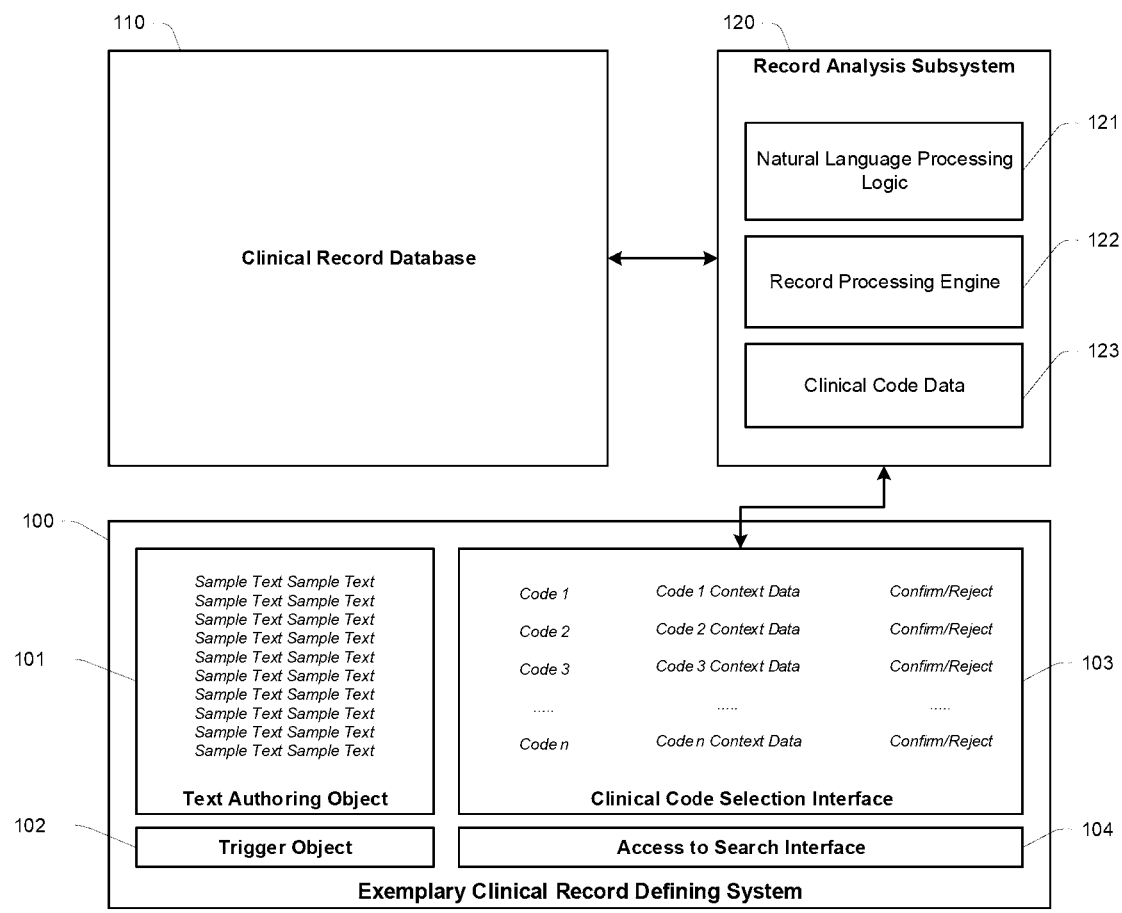
FIG. 1 schematically illustrates a framework according to one embodiment.

Described herein are frameworks and methodologies for enabling categorisation of clinical report data. Embodiments of the invention have been particularly developed to assist categorisation of digitised information, such as clinical report data, in a streamlined manner based on a pre-existing set of classification codes. This, in some embodiments, enables the discovery and extraction of meaningful patterns from unstructured clinical reports. Further embodiments of the invention have been particularly developed to assist in the discovery and extraction of meaningful patterns from an unstructured set of digitised information such as unstructured clinical reports. While some embodiments will be described herein with particular reference to those applications, it will be appreciated that the invention is not limited to such a field of use, and is applicable in broader contexts.

Abstraction Technology

In the context of clinical report management, there is a technical problem to be served in the context of codifying reports based on predefined schema (such as classification codes based on SNOMED CT, ICD, LOINC, and ICD-O3). Typically this is performed by a report Author, or (perhaps more commonly) by an assistant who reviews report data. A partial solution is to provide a search interface which enables an author (or reviewer) to perform searches based on subjective analysis of report content (either at the time of reading or later on). However, this is time-consuming and fraught with error potential. Ideally, computer technology would be applied to enable automated coding, but subjective factors (such as author style and terminology variances) render that somewhat unrealistic. The technology described below provides a technical solution in the form of a particular computer interface which enables a streamlined assistive process towards report coding.

In some embodiments, the technology includes a software component described herein as an "abstractor component". This component is configured to provide automation of abstracting and coding of digitised information. For the purposes clinical text (for example clinical reports, which may include notes and the like). This makes use of a natural language processing (NLP) engine (for example a text analytics engine) that operates in conjunction with (and leverages) a clinical terminology knowledge base. This clinical terminology base provides an expandable intimate knowledge of clinical terminology above, beyond a general purpose natural language processing engine.

The abstractor, in combination with NLP engine and clinical terminology knowledge base, enables concept-based abstracting of clinical records. This allows technology to operate in an objective manner which effectively ignores subjective variance factors such as idiosyncrasies of clinicians' writing styles, and language usage to accurately code records. The abstractor component is in some embodiments configured to operate within an existing software environment, directly interact with an existing software environment (for example via an API), or indirectly interact with an existing software environment (for example via operating system level functionalities).

Various embodiments provide computer implemented methods for enabling categorisation of clinical records. Such methods include identifying a set of user-generated text contained in a user interface object in a user interface environment. For example, in some cases this is: text contained in an active object, such as a specific data field rendered by a given software application; text contained in an active window in third party software; text contained in a referenced file, or the like. In some cases the set of user-generated text includes all text in the object; in other cases it is a reduced selection (for example a user-designated selection, which is for instance made via a highlighting function).

The methods then include processing the set of user-generated text based on a natural language processing engine, being a natural language processing engine leveraging a clinical terminology knowledge base. This knowledge base provides rules and/or relationships to assist in the processing of known medical/clinical terms and expressions based on: known word morphology; sentence parsing; spelling correction; and acronym/abbreviation resolution examples. The knowledge based is preferably updated over time (for example via a lexicon management system) thereby to enable identification of and accounting for additional clinician idiosyncratic authoring styles, and the like.

Based on the processing, a set of one or more suggested classification codes is identified. The classification codes are defined by a pre-existing clinical code structure, such as SNOMED CT, ICD, LOINC, and ICD-O3. In some embodiments multiple code structures are used, and in some cases a user is enabled to select one or more of a set of available code structures (for example via check-boxes or the like). This selection may occur following identification of codes via a user interface component, as discussed below.

Following identification of a set of one or more codes, the methods include causing display of a particular functionally relevant user interface component in the user interface environment. This may in some embodiments be a pop-up window, which is triggered by an external software component. The user interface component is configured to: (i) display the identified set of one or more suggested classification codes; and (ii) enable a user to selectively confirm/reject one or more of the set of identified codes. For example, in a preferred embodiment the user interface component displays, for each identified code, some or all of the following aspects of information:

A section of the code structure to which an identified code belongs.
A disease class associated with an identified code.
A disease stage associated with an identified code. For example, in one embodiment the natural language processing engine is configured to make inferences about the data, for example; inferring a stage of cancer diagnosis.
A disease behaviour associated with an identified code.
A code-structure-specific description associated with an identified code.
A portion of text that triggered the identification of an identified code.
A portion of contextual text including a sub-portion of text that triggered the identification of an identified code. In some embodiments an author is enabled to modify this portion of text in the interface, optionally causing re-processing and re-population of user interface data, and trigger automated updating of the source clinical report text to account for the modification.

This content is preferably displayed in a user-friendly tabulation, which is in some embodiments able to subsequently be stored (or linked to) a file or data set defining a clinical record defined from the source text.

The methods also include receiving input representative of the one or more of the set of identified codes selectively confirmed by the user (for example by confirm/reject check boxes provided via the user interface). This triggers the providing of a signal thereby to cause association of a clinical record including the set of user-generated text with the set of identified codes selectively confirmed by the user. For example, the association may be by way of added textual information, metadata, database level relationships, and so on.

In some embodiments, the user interface component is additionally configured to provide a search interface that enables a user to identify and selectively confirm one or more further codes (which are also associated with the record). For example, an author may notice one or more code descriptors (such as particular diseases) missing, and search for those. This may, in some cases, encourage the author to modify the text, thereby to include material that had been inadvertently omitted (or to correct spelling mistakes and the like).

In some cases, in response to an event whereby a user identifies and selectively confirms one or more further codes, a trigger is initiated thereby to cause updating of the natural language processing engine and/or clinical terminology knowledge base. This may be a manual or automated process, whereby the text is analysed thereby to determine whether there is content that should have caused the automated identification of a manually added clinical code, this resulting in updating of the processing engine and/or clinical terminology knowledge base such that the relevant code is identified in a corresponding situation in future.

It should be appreciated that, in preferred embodiments, the textual language processing engine is configured to identify discrete portions of the text, and, identify a set of one or more suggested classification codes for each discrete portion (as opposed to processing the document as a single whole textual entity). In some embodiments association of the clinical record with the set of identified codes includes defining data that enables association of each discrete portion with its respective classification codes (such that a user is able to identify a particular sub-portion of text that resulted in a given code association).

FIG. 1 illustrates a framework according to one embodiment. In this example, various user interface objects are schematically illustrated as being rendered by an exemplary clinical record system 100. More specifically, these objects are illustrated as being rendered in a common software application, however in further embodiments they are rendered via multiple different software applications (for example using plug-ins and the like).

A user authors text for inclusion in (or defining) a clinical record in object 101. Then, by way of a trigger object (such as a "submit" or "code" button), the text data is provided to a record analysis subsystem 120. Subsystem 120 includes natural language processing logic 121 (which leverages an expandable predefined clinical terminology knowledge base), and a repository of clinical code data (which includes textual description data associated with each of a plurality of clinical code identifiers for one or more clinical coding schema). A record processing engine is configured to coordinate the processing of text data retrieved from system 100, and provide data representative of identified codes for rendering in a user interface object 103.

User interface object 103 provides data representative of identified codes, in this case including, for each identified code, a code descriptor and one or more artefacts of code context data (for example retrieved from code data 123 and/or extracted from the source text from object 101). It also provides confirm/reject controls (which may take the form of checkboxes), thereby to enable user selective confirm/reject command inputs.

A button 103 provides a user with access to a search interface, which enables text-based searching of data 123 thereby to identify one or more further clinical codes manually. In some cases each interface also leverages logic 121 and engine 122 thereby to expand a search string to assist in identification of codes whilst taking into account morphology, spelling, acronyms, and many other language variables.

In the example of FIG. 1, records are stored in a database 110 via subsystem 120. However, in another example, interface 103 is configured to modify text in object 101 (thereby to append clinical codes), or otherwise modify operation of a pre-existing software component that causes recording of a clinical record based on text in object 101 (for example by metadata or database-level association).

Figure 2:
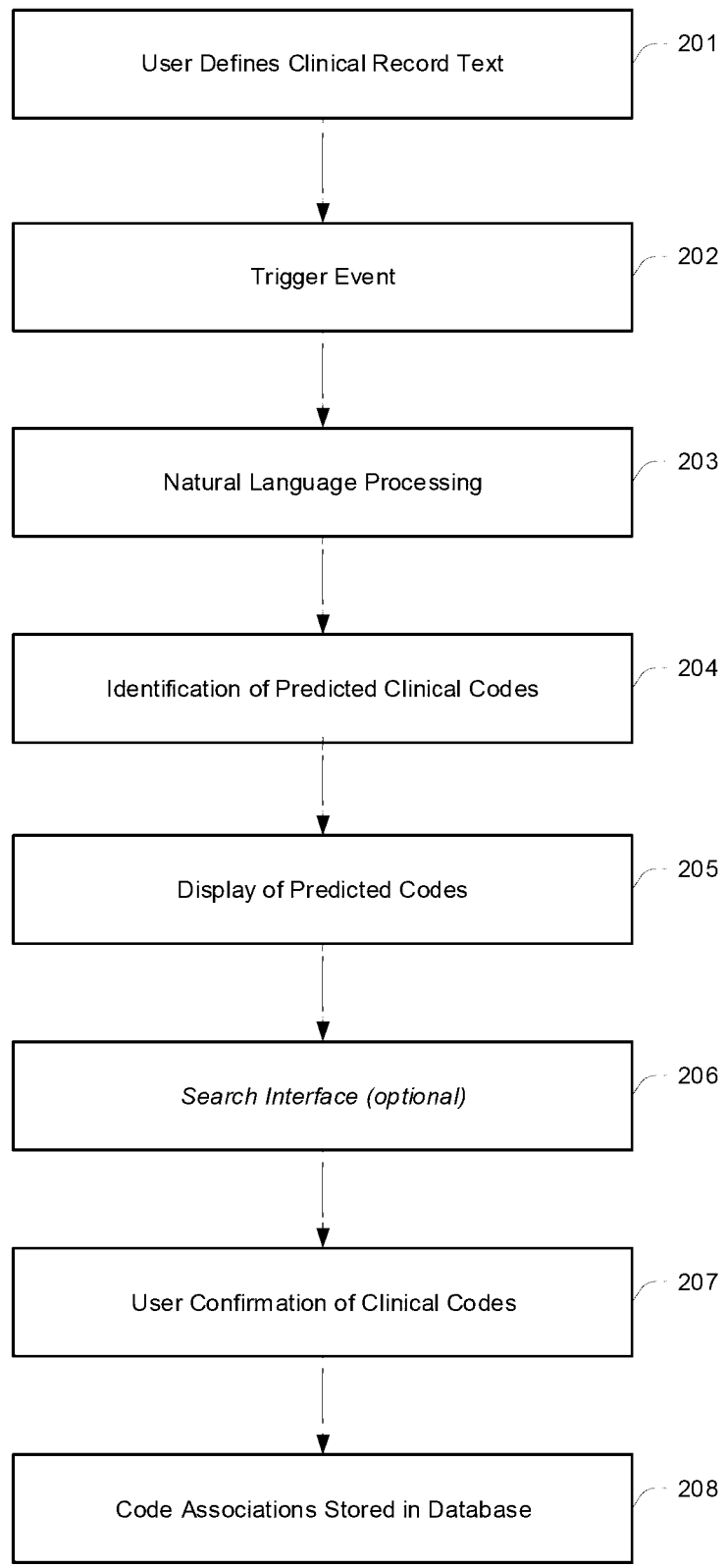
FIG. 2 illustrates a method according to one embodiment.

FIG. 2 illustrates a method according to one embodiment. A user defines clinical record text at 201, and then a trigger event is caused at 202 (for example subject to a user interaction following completion of text authoring). Natural language processing of the text occurs at 203, resulting in identification of one or more predicted/suggested clinical codes at 204. The clinical codes are presented by way of a user interface at 205, which enables user review and selective confirmation. Optionally, at 206, a user accesses a search interface to manually identify and add one or more further codes. User confirmation of codes is received at 207, and the codes and record stored at 208. This may include adding the codes to the text content of a clinical record, and storing that clinical record in a database.

It will be appreciated that the technology described above is not limited to the particular practical implementation environment of clinical record management. For instance, the computer technology in question may be implemented in a variety of other situations where user-defined text requires coding according to a predefined schema.

Concept Search Functionalities

Described below are frameworks and methodologies for enabling searching of clinical report data. Embodiments have been particularly developed to assist in the discovery and extraction of meaningful patterns from unstructured clinical reports. While some embodiments will be described herein with particular reference to that application, it will be appreciated that the invention is not limited to such a field of use, and is applicable in broader contexts.

Various embodiments provide a computer implemented methods for enabling searching of clinical records. For example, this in some cases includes providing a search engine that is configured to access clinical record data provided through one or more clinical systems (or other record generation means). The methods include maintaining access to a database that includes data representative of clinical records. For example, this may be a locally or remotely hosted database, and in some embodiments includes multiple distributed databases.

Each clinical record is pre-processed based upon a natural language processing engine, thereby to associate the record with one or more clinical codes 9 for example via technology described further above). These clinical codes are, at least in some examples, defined in a clinical code hierarchical structure. An example of a clinical code hieratical structure used in some embodiments is SNOMED CT. Other code structures include ICD, LOINC, and ICD-O3. In some embodiments there is a plurality of clinical code hierarchical structures, and a user is enabled to select one or more of these to be used for the purpose of a given query.

The natural language processing engine preferably accounts factors such as word morphology, sentence parsing, spelling correction, synonym, metonym, acronym and abbreviation resolution, document structure thereby to enable mapping of records to codes in spite of a wide range of language variations that may be observed in clinical records. The natural language processing engine is configured to be updated (and re-run over some or all of the records) over time, thereby to improve its effectiveness.

A search interface is provided, for example in a manner enabling rendering of a query-defining interface at a client terminal. Such an interface configured to enable user input of query parameters. These query parameters include text-based concept-defining data, for example "breast cancer" or the like.

A query processing engine is configured to process the text-based concept-defining data based on a predefined protocol thereby to identify one or more clinical codes associated the concept-defining data. For example, factors such as word morphology, sentence parsing, spelling correction, acronym and abbreviation resolution are handled by such a protocol, which is configured to map various instances of concept-defining data to codes, even if there is no direct textual relationship between a code descriptor and the concept-defining data itself. In some embodiments the concept-defining data is defined by a text-based set of search terms (for example a search string), which only one representation of the semantics of a concept, being a concept that is in effect searched as described herein. For example, the concept-defining data provides a single representation of a concept that has an non-enumerable set of representations In overview, the query processing engine is configured to identify one or more clinical records that are associated with the same clinical codes as a concept represented by the instance of the concept-defining data. In this regard, there is a dual-level expansion process:

Firstly, expansion in relation to the text of a clinical record thereby to associate it with codes based on natural language processing; and Secondly, expansion at the concept-defining data end to identify relevant codes.

By way of example, consider the following:

A report may includes a term "Term A".

Based on enhanced NLP-based processing, that term is determined to match "Term B" (for example they are determined to be equivalents.

Term B is associated with Code X.

A query includes Term C.

Term C is processed also found to be associated with Code X. This may include processing that associates Term C with Term B term via enhanced NLP-based processing, before arriving at the association with Code X.

Examples of Term A, B and C might be "Lentigo Maligna", "melanoma" and "skin cancer".

The above example, a search using Term C is executed to identify the record containing Term A, on the basis that they both match Term B of Code X. This provides a significant technical advantage over conventional searching technology, on the basis that term C and Term A might not be directly relatable.

In some embodiments the method additionally includes associating with the concept-defining data one or more further clinical codes, wherein the one or more further clinical codes are sub-tree codes to the identified one or more clinical codes in the hierarchical structure. For example, the search interface is configured to enable the user to select whether or not to perform the process of additionally associating with the concept-defining data one or more further clinical codes, wherein the one or more further clinical codes are sub-tree codes to the identified one or more clinical codes in the hierarchical structure. An example in the context of medical terminology is "breast cancer" which has the sub-type "infiltrating ductal carcinoma".

FIG. 1 illustrates a framework according to one embodiment. A plurality of clinical records defining systems 500 include an exemplary client terminal 500'. These are each optionally used to define clinical record data. This data is provided to a central clinical record database 510. Systems 500 may include various software platforms used to generate clinical report content. A record analysis subsystem includes a record processing engine 532, which is configured to maintain access to database 510, and process records therein based on natural language processing logic 531. More specifically, this processing enables each record to be associated with one or more clinical codes, based on clinical code data 533. Record processing engine 532 is preferably configured to process newly added records, and to re-process existing records following updates to logic 531 and/or data 533.

A search engine subsystem 530 is configured to process queries submitted from client terminals 550, including an exemplary client terminal 550'. The client terminals in some embodiments provide search interfaces via proprietary software, or in some cases via web-browser delivered interfaces.

FIG. 2 illustrates exemplary methods 600 and 610. Method 600 is a method for natural language processing of clinical record data thereby to enable association with codes (such as SNOMED CT codes), whereas method 610 is a query processing method.

In relation to method 600, functional block 601 represents a process including identifying a clinical record for processing. For example this may be a newly submitted record, or a record queued for periodic re-processing (for example based on updated processing logic). Functional block 602 represents a process including application of natural language processing logic, which enables association of the record to codes (such as SNOMED CT codes), whilst resolving amongst other things word morphology, sentence parsing, spelling correction, acronym and abbreviation resolution. Code associations are stored in the database at 604.

In relation to method 610, functional block 611 includes receiving a query. The query is processed thereby to identify codes (such as SNOMED CT codes) at 612, again resolving issues such as word morphology, sentence parsing, spelling correction, acronym and abbreviation resolution. This enables translation between terms used by a query submitting user, and terms actually present in code descriptors. As represented by functional block 613, is the user a selected an option for an "expended" query, then sub-tree codes are also determined. Functional block 614 represents a process including identifying those records associated with the same codes (and, where relevant, sub-tree codes).

Figure 4:
FIG. 4 illustrates a search interface according to one embodiment.
Figure 5:
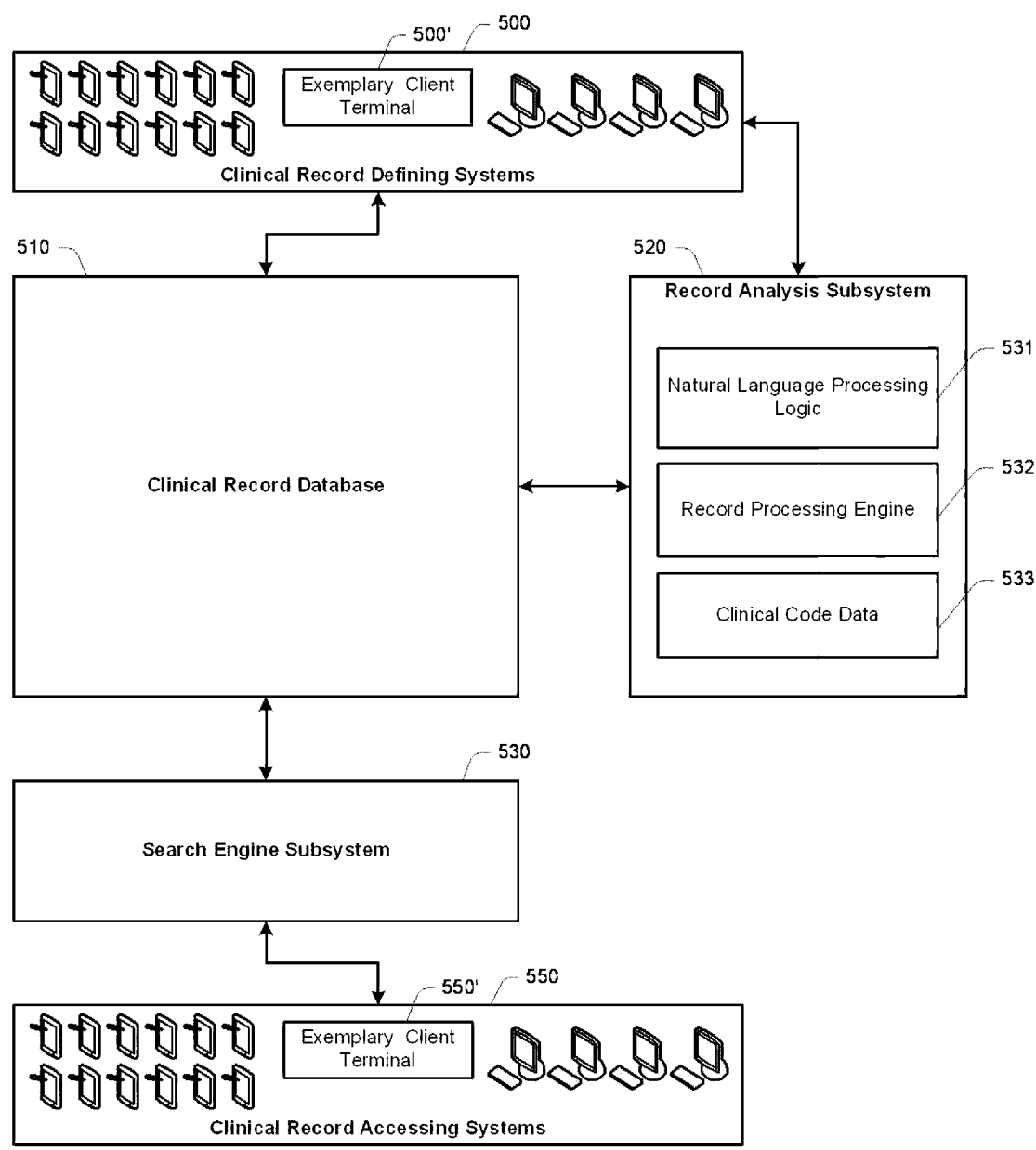
FIG. 5 schematically illustrates a framework according to one embodiment.
Figure 6:
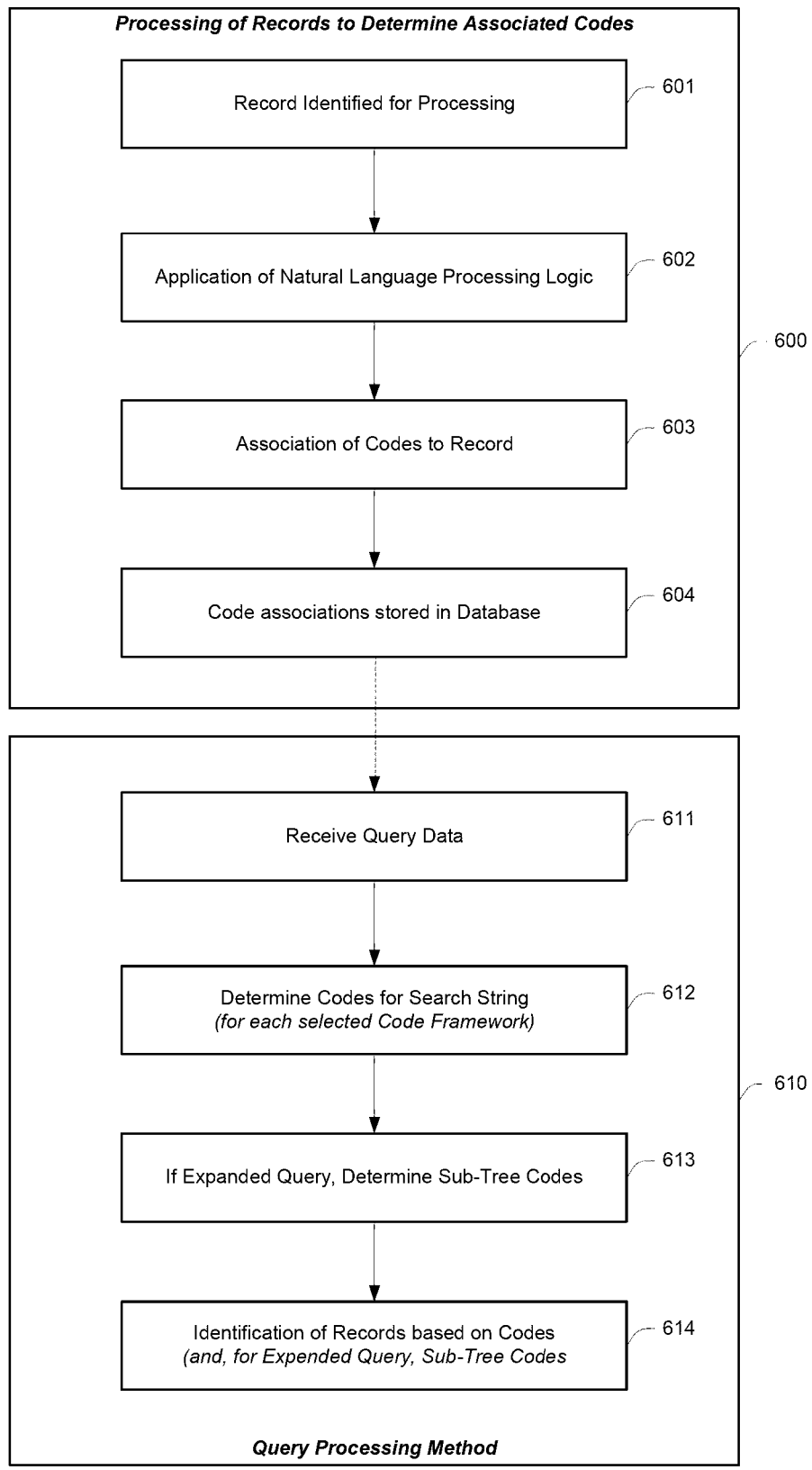
FIG. 6 illustrates a method according to one embodiment.
Figure 7:
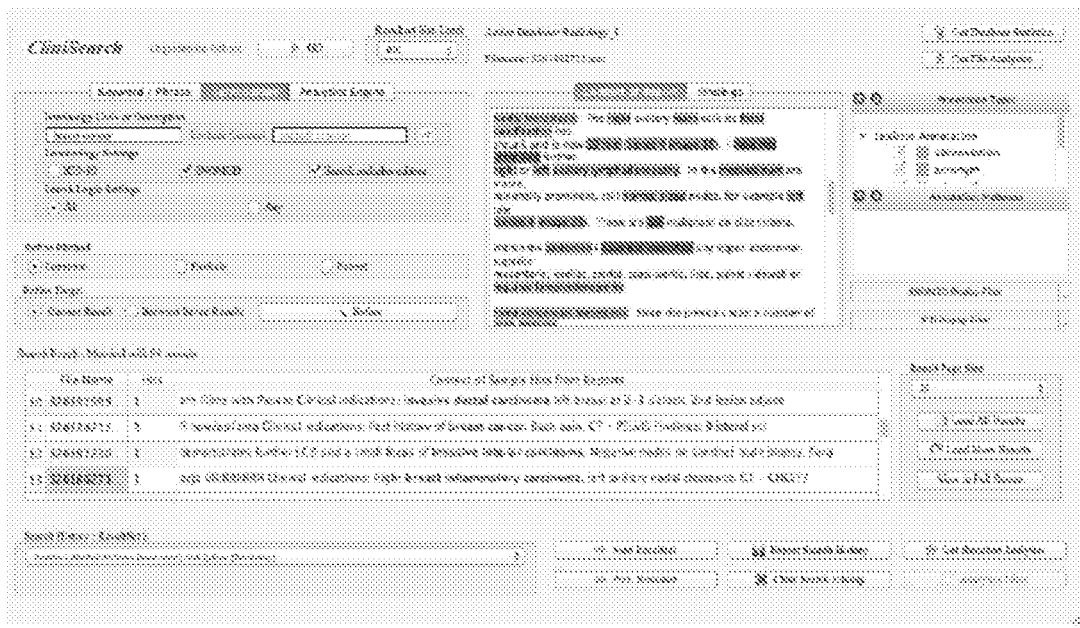
FIG. 7 illustrates a search interface according to one embodiment.

FIG. 4 illustrates an exemplary query interface. In this example, a user inputs a concept-defining data in a "terminology code or description" field, and may also input excluded concepts. The user also selects codes to be considered (in this case being ICD-10 and/or SNOMED), and optionally selects whether a sub-tree search is to be performed. The user also selects whether "any" or "all" type search logic is to be applied. Various options for search refining/combining are also provided. In the illustrated embodiment, search results are displayed along with a window that displays content of a selected search result.

It will be appreciated that technology described herein is readily configured to assist in discovering and extracting meaningful patterns (analytics) in patient data within unstructured clinical reports. These are able to provide fast search speed and precision extraction, using combinations of multiple search algorithms and language processing techniques to maximise the coverage and reliability of results, may co-ordinate with any search engine to multiply the value of locally developed expertise, and can retrieve reports in tandem with structured retrieval queries to collect variable data types into the one location.

The use of a concept-based search mechanism enables understanding of the idiosyncrasies of clinicians' writing styles and language usage, thereby to accurately collect desired data. In some embodiments the technology is configured to extract the appropriate content for either display in a user-friendly tabulation or export to a CSV file for subsequent processing by combining a variety of facts in a report. Furthermore, it is in some embodiments set up to produce tailored reports to support each organisation's specific needs.

In some embodiments efficacy is improved by updating natural language processing logic by tuning it to local content in a process of training it to understand the writing vagaries of local authors. Natural language engine resolving amongst other things word morphology, sentence parsing, spelling correction, acronym and abbreviation resolution.

Concept processing may include identifying any text equivalent in a concept-defining data to ICD, LOINC, O3 and SNOMED CT codes (and in some cases proprietary dictionaries).

Extractions may include disease, disorders, procedures, with special attention to cancer details for primaries, metastases and nodes. Document analytics may be performed, including classification of documents from their contents such as for tumour stream or report purpose.

In some embodiments external reuse of extractions & inferences is provided, for example including buttons to export extracted content to CVS files for delivery to researchers or search collections.

In some embodiments workflow ease is assisted by providing a search history, batch processing and results export so as to assemble a workflow and operate it entirely automatically thus supporting periodic reporting.

In some embodiments a mechanism is provided to capture content that is not processed initially can be used to lodge that content into the knowledge repository so it is not missed again.

Some embodiments provide automatic despatch of files to registered users when a record of interest is created in the system.

Embodiments may, by way of example, be applied in the following environments:

Patient Studies (for example to recruit a common cohort or phenotypes for clinical trials; to target particular disease classes for research; to alert staff when a pertinent record is created in the storage system).

Auditing Clinical Records (for example to check the accuracy of clinical coding across disease classes; to semi-automate codification for billing; to identify and understand the case mix of a particular organisation).

Research (for example to answer ad-hoc questions about the distributions of disease morbidities).

Assessing Training & Report Writing (for example to investigate report reliability and readability; to provide feedback to staff on the nature of their written composition; to tutor and evaluate the work of trainees; to compile activity reports for professional associations for registration; to investigate more effective systematic methods for preparing reports).

It will be appreciated that these technologies overcome technical problems associated with automated searching and/or processing of authored report data, where that data include idiosyncratic and/or subjectively defined elements.

Example Client-Server Framework

Figure 3:
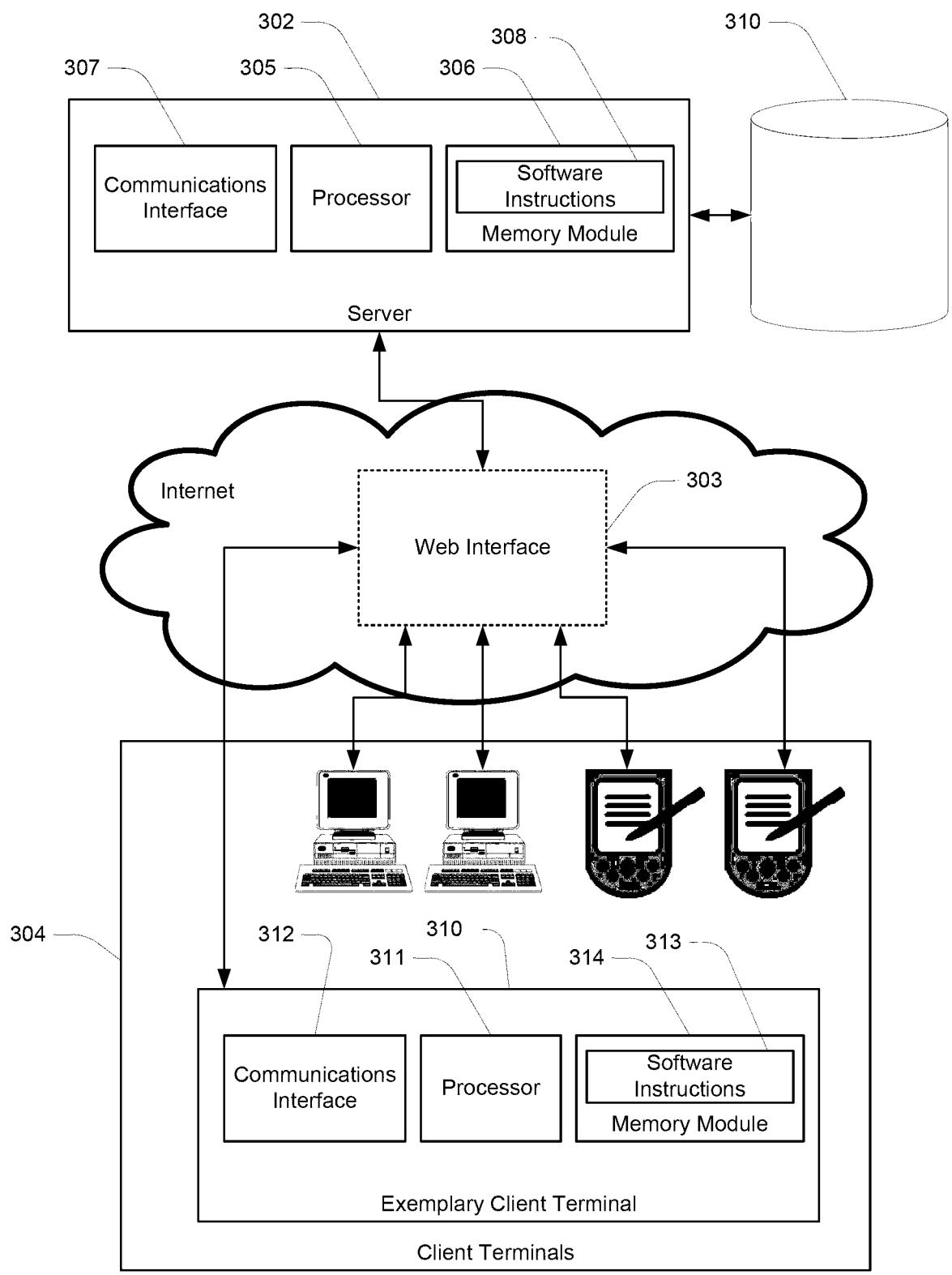
FIG. 3 illustrates an exemplary client-server framework.

In some embodiments, methods and functionalities considered herein are implemented by way of a client-server framework, as illustrated in FIG. 3. In overview, a web server 302 provides a web interface 303. This web interface is accessed by the parties by way of client terminals 304. In overview, users access interface 303 over the Internet by way of client terminals 304, which in various embodiments include the likes of personal computers, PDAs, cellular telephones, gaming consoles, and other Internet enabled devices.

Server 303 includes a processor 305 coupled to a memory module 306 and a communications interface 307, such as an Internet connection, modem, Ethernet port, wireless network card, serial port, or the like. In other embodiments distributed resources are used. For example, in one embodiment server 302 includes a plurality of distributed servers having respective storage, processing and communications resources. Memory module 306 includes software instructions 308, which are executable on processor 305.

Server 302 is coupled to a database 310. In further embodiments the database leverages memory module 306.

In some embodiments web interface 303 includes a website. The term "website" should be read broadly to cover substantially any source of information accessible over the Internet or another communications network (such as WAN, LAN or WLAN) via a browser application running on a client terminal. In some embodiments, a website is a source of information made available by a server and accessible over the Internet by a web-browser application running on a client terminal. The web-browser application downloads code, such as HTML code, from the server. This code is executable through the web-browser on the client terminal for providing a graphical and often interactive representation of the website on the client terminal. By way of the web-browser application, a user of the client terminal is able to navigate between and throughout various web pages provided by the website, and access various functionalities that are provided.

Although some embodiments make use of a website/browser-based implementation, in other embodiments proprietary software methods are implemented as an alternative. For example, in such embodiments client terminals 304 maintain software instructions for a computer program product that essentially provides access to a portal via which framework 100 is accessed (for instance via an iPhone app or the like).

In general terms, each terminal 304 includes a processor 311 coupled to a memory module 313 and a communications interface 312, such as an internet connection, modem, Ethernet port, serial port, or the like. Memory module 313 includes software instructions 314, which are executable on processor 311. These software instructions allow terminal 304 to execute a software application, such as a proprietary application or web browser application and thereby render on-screen a user interface and allow communication with server 302. This user interface allows for the creation, viewing and administration of profiles, access to the internal communications interface, and various other functionalities.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

What is claims is:

1. A computer implemented method for enabling searching of clinical records the method including:
   maintaining access to a database that includes data representative of clinical records, wherein each clinical record includes text content which provides a single representation of the semantics of a concept that has a non-enumerable set of representations and is pre-processed based upon a natural language processing engine, wherein the natural language processing engine leverages a clinical terminology knowledge base including rules and relationships between terms and expressions for processing of word morphology and sentence parsing, wherein to process each clinical record, the natural language processing engine: processes a portion of the text content of the clinical record based on the rules and relationships; resolves word morphology and sentence parsing in the portion of the text content; and abstracts the semantics of the concept represented by the portion of text content thereby to translate between terms present in the portion of text content and terms associated with clinical codes; identifies any text in the portion of text content equivalent to terms of a respective clinical code; and maps the record to the respective clinical code even where there is no direct textual relationship between a code descriptor and the text portion, thereby to associate at least one of the records having an exemplary term A with an exemplary clinical code X on the basis that exemplary term A is equivalent to an exemplary term B of the exemplary clinical code X, wherein the exemplary clinical code X is defined in a clinical code hierarchical structure, thereby providing a first level of expansion by abstracting the clinical records;
   receiving a search query from an interface that is configured to enable user input of search query parameters, wherein the search query parameters include text-based concept-defining data which provides a single representation of the semantics of a concept that has a non-enumerable set of representations, wherein the search query includes an exemplary term C;
   processing the text-based concept-defining data based upon the natural language processing engine by: processing a search string of the text-based concept defining data representing the semantics of the concept based on the rules and relationships; resolving word morphology and sentence parsing in the search string; and abstracting the semantics of the concept represented by the search string thereby to translate between terms present in the search string and terms associated with clinical codes; identifying any text in the search string equivalent to terms of a respective clinical code; and mapping the concept defining data to the respective clinical code even where there is no direct textual relationship between a code descriptor and the search string, thereby to identify the exemplary clinical code X on the basis that the exemplary term C is equivalent to exemplary term B, thereby providing a second level of expansion by abstracting the search query;
   identifying the at least one clinical record having the exemplary term A on the basis that it is associated with the same exemplary clinical code X as the concept-defining data having the exemplary term C, even in circumstances where exemplary term C is not directly relatable to exemplary term A;
   displaying, on the interface, a portion of contextual text of a source clinical record, the portion of contextual text including a sub-portion of text that triggered association of an associated code with the source clinical record, enabling a user to modify the portion of contextual text, re-processing the portion of contextual text, and triggering automated updating of the source clinical record to account for the modification; and
   enabling the user to manually identify and associate one or more further clinical codes with a given clinical record, and in response to the user associating the one or more clinical codes with the given record, updating the natural language processing engine and clinical terminology knowledge base such that the relevant one or more clinical codes is automatically identified and associated with other clinical records in a corresponding situation in future.

2. A method according to claim 1 including additionally associating with the concept-defining data one or more further clinical codes, wherein the one or more further clinical codes are sub-tree codes to the identified one or more clinical codes in the hierarchical structure.

3. A method according to claim 2 wherein the interface is configured to enable the user to select whether or not to perform the process of additionally associating with the concept-defining data one or more further clinical codes, wherein the one or more further clinical codes are sub-tree codes to the identified one or more clinical codes in the hierarchical structure.

4. A method according to claim 1, wherein there is a plurality of clinical code hierarchical structures.

5. A method according to claim 4 wherein the interface is configured to enable the user to select one or more of the plurality of clinical code hierarchical structures for a given query.

6. A computer implemented method for enabling categorisation and searching of clinical records, the method including:
   identifying a set of user-generated text contained in a user interface object in a user interface environment;
   processing the set of user-generated text based on a natural language processing engine, wherein the natural language processing engine leverages a clinical terminology knowledge base;
   based on the processing, identifying a set of one or more suggested classification codes, wherein the classification codes are defined by a pre-existing clinical code structure;
   causing display of a user interface component in the user interface environment, wherein the user interface component: (i) displays the identified set of one or more suggested classification codes; and (ii) enables a user to selectively confirm/reject one or more of the set of identified codes;
   receiving input representative of the one or more of the set of identified codes selectively confirmed by the user;

providing a signal thereby to cause association of a clinical record including the set of user-generated text with the set of identified codes selectively confirmed by the user maintaining access to a database that includes data representative of clinical records, wherein each clinical record includes text content which provides a single representation of the semantics of a concept that has a non-enumerable set of representations and is pre-processed based upon the natural language processing engine, wherein the natural language processing engine leverages the clinical terminology knowledge base including rules and relationships between terms and expressions for processing of word morphology and sentence parsing, wherein to process each clinical record, the natural language processing engine: processes a portion of the text content of the clinical record based on the rules and relationships; resolves word morphology and sentence parsing in the portion of the text content; and abstracts the semantics of the concept represented by the portion of text content thereby to translate between terms present in the portion of text content and terms associated with clinical codes;

identifies any text in the portion of text content equivalent to terms of a respective clinical code; and maps the record to the respective clinical code even where there is no direct textual relationship between a code descriptor and the text portion, thereby to associate at least one of the records having an exemplary term A with an exemplary clinical code X on the basis that exemplary term A is equivalent to an exemplary term B of the exemplary clinical code X, wherein the exemplary clinical code X is defined in a clinical code hierarchical structure, thereby providing a first level of expansion by abstracting the clinical records;

receiving a search query from an interface that is configured to enable user input of search query parameters, wherein the search query parameters include text-based concept-defining data which provides a single representation of the semantics of a concept that has a non-enumerable set of representations, wherein the search query includes an exemplary term C;

processing the text-based concept-defining data based upon the natural language processing engine by: processing a search string of the text-based concept defining data representing the semantics of the concept based on the rules and relationships; resolving word morphology and sentence parsing in the search string; and abstracting the semantics of the concept represented by the search string thereby to translate between terms present in the search string and terms associated with clinical codes; identifying any text in the search string equivalent to terms of a respective clinical code; and mapping the concept defining data to the respective clinical code even where there is no direct textual relationship between a code descriptor and the search string, thereby to identify the exemplary clinical code X on the basis that the exemplary term C is equivalent to exemplary term B, thereby providing a second level of expansion by abstracting the search query;

identifying the at least one clinical record having the exemplary term A on the basis that it is associated with the same exemplary clinical code X as the concept-defining data having the exemplary term C, even in circumstances where exemplary term C is not directly relatable to exemplary term A;

displaying, on the interface, a portion of contextual text of a source clinical record, the portion of contextual text including a sub-portion of text that triggered association of an associated code with the source clinical record, enabling a user to modify the portion of contextual text, re-processing the portion of contextual text, and triggering automated updating of the source clinical record to account for the modification; and enabling the user to manually identify and associate one or more further clinical codes with a given clinical record, and in response to the user associating the one or more clinical codes with the given record, updating the natural language processing engine and clinical terminology knowledge base such that the relevant one or more clinical codes is automatically identified and associated with other clinical records in a corresponding situation in future.

7. A computer system configured to perform a method according to claim 1.

8. A non-transitory carrier medium carrying computer executable code that, when executed on a processor, causes the processor to perform a method according to claim 1.

* * * * *